US009034960B2

(12) United States Patent
Brown et al.

(10) Patent No.: US 9,034,960 B2
(45) Date of Patent: May 19, 2015

(54) ANTIDRIFT COMPOSITION

(75) Inventors: William L. Brown, Pleasantville, NY (US); George A. Policello, Ossining, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 168 days.

(21) Appl. No.: 13/558,513

(22) Filed: Jul. 26, 2012

(65) Prior Publication Data

US 2014/0031467 A1 Jan. 30, 2014

(51) Int. Cl.

| | |
|---|---|
| ***C08K 5/544*** | (2006.01) |
| ***C08L 33/26*** | (2006.01) |
| ***A01N 57/20*** | (2006.01) |

(52) U.S. Cl.

CPC ................. *A01N 57/20* (2013.01); *C08L 33/26* (2013.01); *C08K 5/544* (2013.01)

(58) Field of Classification Search

USPC .......................................................... 524/188

See application file for complete search history.

(56) References Cited

U.S. PATENT DOCUMENTS

| | | | |
|---|---|---|---|
| 3,842,022 | A | 10/1974 | Wang |
| 4,035,479 | A | 7/1977 | George, Jr. et al. |
| 4,102,667 | A | 7/1978 | Robinson et al. |
| 4,266,962 | A | 5/1981 | Kersting et al. |
| 4,510,081 | A | 4/1985 | Bronner et al. |
| 4,610,311 | A | 9/1986 | Bronner et al. |
| 5,529,975 | A | 6/1996 | Chamberlain |
| 5,550,224 | A | 8/1996 | Hazen |
| 5,558,806 | A | 9/1996 | Policello et al. |
| 5,824,797 | A | 10/1998 | Hazen |
| 5,874,096 | A | 2/1999 | Hazen |
| 5,964,917 | A | 10/1999 | Latting |
| 6,051,730 | A | 4/2000 | Pallas et al. |
| 6,060,522 | A | 5/2000 | Pallas et al. |
| 6,288,010 | B1 | 9/2001 | Rose et al. |
| 6,358,294 | B1 | 3/2002 | Latting |
| 6,391,962 | B2 | 5/2002 | Zerrer et al. |
| 6,423,109 | B2 | 7/2002 | Brigance et al. |
| 6,534,563 | B1 | 3/2003 | Bergeron et al. |
| 6,878,180 | B2 | 4/2005 | Sexton et al. |
| 7,507,775 | B2 | 3/2009 | Leatherman et al. |
| 7,645,720 | B2 | 1/2010 | Leatherman et al. |
| 7,652,072 | B2 | 1/2010 | Leatherman et al. |
| 7,700,797 | B2 | 4/2010 | Leatherman et al. |
| 7,872,053 | B2 | 1/2011 | Wagner et al. |
| 7,879,916 | B2 | 2/2011 | Leatherman et al. |
| 7,935,842 | B2 | 5/2011 | Policello et al. |
| 8,008,231 | B2 | 8/2011 | Leatherman et al. |
| 8,183,317 | B2 | 5/2012 | Leatherman et al. |
| 2002/0006874 | A1 | 1/2002 | Brigance et al. |
| 2004/0058821 | A1 | 3/2004 | Brigance et al. |
| 2007/0131611 | A1 | 6/2007 | Peng et al. |
| 2007/0281929 | A1 | 12/2007 | Amanokura et al. |
| 2008/0161219 | A1 | 7/2008 | Ohlhausen et al. |
| 2009/0298695 | A1 | 12/2009 | Wu et al. |

FOREIGN PATENT DOCUMENTS

| | | | | |
|---|---|---|---|---|
| CN | 102 523 811 | A | 7/2012 | |
| JP | 7053292 | A | 2/1995 | |
| WO | 95/08916 | A1 | 4/1995 | |
| WO | 2005/073556 | A1 | 8/2005 | |
| WO | WO 2005/073556 | A1 * | 8/2005 | ............. F04B 19/24 |
| WO | 2012/076567 | A2 | 6/2012 | |

OTHER PUBLICATIONS

Halt "Drift Reduction Agent", AGSPRAY Agricultural Solutions; URL:http://www.agsprayinc.com/data/halt_lab.pdf; XP55055810; Apr. 11, 2009, pp. 1-1.

Database WPI Week 201267 Thomson Scientific, London, GB; AN 2012-K43906; XP002693458.

Database CA [Online] Chemical Abstracts Service, Columbus, Ohio, US; Jul. 9, 2012, Zou, Yingbin et al; "Method for applying chemical nitrogen fertilizer under crop no-tillage cultivation conditions", XP002693459, retrieved from STN Database accession No. 2012:973279 abstract.

Database WPI Week 199517 Thomson Scientific, London, GB; AN 1995-128181 XP002693460.

Database CA [Online] Chemical Abstracts Service, Columbus, Ohio, US; Apr. 29, 1995, Takahashi, Shigeru et al; "Manufacture of fertilizer in the form of paste", XP002693461, retrieved from STN Database accession No. 1995:516430 abstract.

International Search Report and Written Opinion dated Mar. 27, 2013.

* cited by examiner

*Primary Examiner* — Robert Harlan

(74) *Attorney, Agent, or Firm* — Dominick G. Vicari; Joseph S. Ostroff

(57) ABSTRACT

A solid, water-soluble fast-dissolving antidrift composition includes a urea-based complex-forming component (i) complexed with an antidrift component (ii), the antidrift composition optionally further including an adjuvant component (iii).

13 Claims, 1 Drawing Sheet

Modified Spray Booth
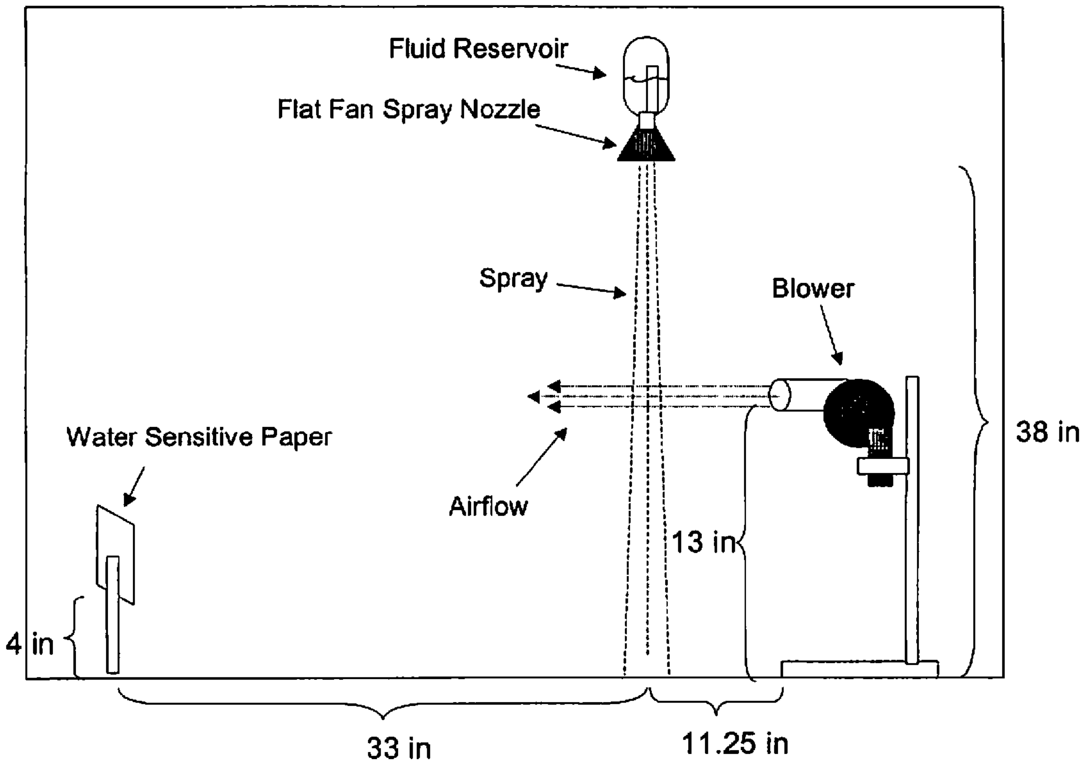

ANTIDRIFT COMPOSITION

FIELD OF THE INVENTION

This invention relates to complexes of urea-based complex-forming compounds and antidrift agents for controlling the droplet size of aqueous sprays, particularly those intended for agricultural use.

BACKGROUND OF THE INVENTION

Spray drift, or off-target drift, is an increasingly important concern of the agricultural industry. Spray drift is the movement of herbicides or other sprayed agricultural treatment material away from the target area resulting in wasted material, possible damage to nearby crops and plants and/or pollution of local surface water. When agricultural compositions are sprayed onto crops, a drop size distribution results. While small drops, typically defined as less than 150 microns, traditionally provide better crop coverage, they are also more prone to drifting. Large drops, commonly regarded as those with diameters greater than 400 microns, tend to resist drift but are prone to bouncing off crop surfaces resulting in reduced coverage and effectiveness. The optimum drop size range for minimizing drift and maximizing deposition effectiveness is generally considered to be 200-400 microns.

Reducing the amount of small droplets can significantly reduce spray drift. This is currently being achieved by employing new nozzle technology or through the use of relatively high molecular weight water-soluble polymers as antidrift agents. Antidrift additives include acrylamide homopolymers and copolymers, polysaccharides such as guar, guar derivatives and xanthan gums and polyalkylene oxides such as polyethylene oxides. One problem with these and other known antidrift additives is that they are often difficult to dissolve in water. A second problem is that the larger drops that they produce tend not to adhere well to the target crops.

SUMMARY OF THE INVENTION

In accordance with the present invention, a solid, water-soluble, fast-dissolving antidrift composition is provided which comprises a urea-based complex-forming component (i) complexed with an antidrift component (ii).

The antidrift composition of this invention when incorporated in an aqueous spray formulation, e.g., one employed in agriculture, provides drift reduction properties very similar to those of its non-complexed antidrift component (ii). However, unlike difficult-to-dissolve non-complexed antidrift component (ii), when antidrift component (ii) is complexed with urea-based complex forming component (i), the antidrift composition herein greatly decreases the amount of mixing time required to dissolve its complexed antidrift component (ii) in the aqueous spray composition. As a further advantage, when added to an agricultural spray, urea-based complex-forming component (i) of the antidrift composition provides a source of fertilizer apart from and in addition to any other fertilizer(s) with which the antidrift composition may be combined.

BRIEF DESCRIPTION OF THE DRAWING

FIG. 1 is a schematic illustration of the spray booth apparatus employed herein for measuring spray drift.

DESCRIPTION OF THE INVENTION

In the specification and claims that follow, certain terms and expressions shall be understood as having the designated meanings.

The singular forms “a”, “an” and “the” include the plural unless the context clearly indicates otherwise.

As used herein, the term “may” indicates a possibility of an occurrence within a set of circumstances; a possession of a specified property, characteristic or function; and/or qualifies another verb by expressing one or more of an ability, capability, or possibility associated with the qualified verb. Accordingly, usage of “may” indicates that a modified term is apparently appropriate, capable, or suitable for an indicated capacity, function or usage while taking into account that in some circumstances the modified term may sometimes not be appropriate, capable or suitable. For example, in some circumstances an event or capacity can be expected, while in other circumstances the event or capacity does not or cannot occur, such distinction being captured by the term “may”.

All ranges in the specifications and claims are inclusive of the endpoints and are independently combinable. It will be understood that any numerical range recited herein is intended to include all sub-ranges within that range and any combination of the various endpoints of such ranges or sub-ranges.

The term “solid” as it applies to the antidrift composition of the invention shall be understood as including an essentially water-free composition as well as one containing a small amount of water, e.g., ranging from a negligible amount up to 10% by weight water and even higher, provided the water-containing composition exhibits a solid appearance and when provided in a particulate form, e.g., powder, granules, pellets, prills, or the like, exhibits some degree of flowability.

The expression “water-soluble” shall be understood herein to be synonymous with “water-dispersible”.

The expression “fast-dissolving” shall be understood to refer to that characteristic property of the antidrift composition of the invention whereby a given quantity of the antidrift composition in particulate form will achieve complete dissolution in an aqueous medium in significantly less time, e.g., in at least 30%, preferably in at least 50% and more preferably in at least 70%, less time than an equivalent amount of a mechanical mixture, i.e., a non-complexed mixture, of urea-based complex-forming component (i) and antidrift component (ii), each of comparable particulate form, under substantially identical dissolution conditions.

The term “complex” as used herein shall be understood to be synonymous with “clathrate”, “clathrate complex”, “cage compound”, “host-guest complex”, “inclusion compound”, “inclusion complex”, and “adduct” as these terms and expressions are understood in the art. While the precise nature of the antidrift-containing complex of the invention is not known with certainty, the complex exhibits properties that differ from a simple mechanical mixture of its urea-based complex-forming component (i) and antidrift component (ii).

The term “adjuvant” as used herein refers to any optional component that when incorporated in the antidrift composition of the invention imparts a functionally useful property thereto, e.g., dispersing, wetting, spreading, etc., and/or enhances a functionally useful property already possessed in some degree by the antidrift composition.

The term “superspreader” as used herein refers to those adjuvant surfactants that have the property of “superspreading”, or “superwetting”. Superspreading/superwetting is the ability of a drop of a solution of a superspreader surfactant to spread to a diameter that is greater than the diameter of a drop of distilled water on a hydrophobic surface, and also greater than the diameter to which a solution of water and non-superspreading surfactant spreads on the hydrophobic surface. In addition to this difference in spread diameter, the contact angle of a drop of superspreader surfactant solution on a surface is larger than that of a non-superspreading surfactant solution on the same surface.

As previously indicated, the antidrift composition of this invention is a solid water-soluble complex of urea-based complex-forming component (i), i.e., the "host" of a "host-guest" complex with antidrift component (ii) as the "guest" of the "host-guest" complex. Each of these components of the antidrift composition herein, ranges of their amounts in the antidrift composition, general methods for the preparation of the antidrift composition and specific examples illustrating various embodiments of the antidrift composition and their application will now be described.

A. Components of the Antidrift Composition

1. Urea-Based Complex-Forming Component (i)

Urea Based Complex-Forming component (i) of the antidrift composition of the invention can be selected from at least one of urea and urea derivative capable of forming a complex with antidrift component (ii). Among the urea-based complex-forming urea derivatives that can be used herein with generally good results are thiourea, urea formaldehyde, urea hydrate, urea phosphate and urea sulfate (monocarbamide dihydrogen sulfate).

Employing urea and/or any complex-forming urea derivative, including any of those aforementioned, complexed with antidrift component (ii) has the advantages of rendering the typically difficult-to-dissolve antidrift component (ii) more readily dissolved in the intended aqueous spray composition and where such spray composition is to be used in agriculture, providing a significant source of fertilizer. Urea phosphate additionally provides a source of phosphate and urea sulfate may additionally function as an herbicide, again, in the case of an agricultural spray.

2. Antidrift Component (ii)

Antidrift component (ii) of the antidrift composition of the invention can be selected from among any of the known antidrift agents including, without limitation, polymeric antidrift agents such as polysaccharides, acrylamide homopolymers and copolymers and their salts, e.g., their alkali metal salts, in particular, those of sodium and potassium, their ammonium salts, their di- and trialkylamine salts, their di- and trialkanolamine salts, and the like, copolymers of maleic acid and conjugated diene including their salts such as those aforementioned, polyalkylene oxides such as polyethylene oxide, polypropylene oxide and poly(ethylene oxide-co-propylene oxide), polyvinylpyrrolidone, and their mixtures. These and other known types of polymeric drift agents are generally of relatively high molecular weight, e.g., on the order of from 10,000 to 50,000,000, and preferably from 100,000 to 25,000,000, weight average molecular weight.

Specific examples of useful polysaccharide antidrift agents include guar, guar derivatives such as hydroxylpropyl guar (HPG), carboxymethyl hydroxypropyl guar (CMHPG), xanthan gum, and mixtures thereof.

Specific examples of acrylamide polymers include polyacrylamide homopolymers and polyacrylamide copolymers and their alkali metal salts such as poly(acrylamide-co-acrylic acid), poly(acrylamide-co-acrylic acid, Na salt), polyacrylamidoalkylsulfonic acid salts, and mixtures thereof.

Among the useful polyalkylene oxides are the polyethylene oxides and mixtures thereof.

3. Optional Adjuvant Component (iii)

The antidrift composition of the invention can optionally contain one or more adjuvant components (iii) known for incorporation in aqueous agricultural sprays. One or more of these optional adjuvant components (iii) may be admixed with urea-based complex-forming component (i) and/or antidrift component (ii) prior to forming the complex resulting in the antidrift composition of the invention thus offering the possibility that depending on its identity, some or all of a particular adjuvant component (iii) may also be complexed by urea-based complex-forming component (i). In addition to or in lieu of the foregoing, one or more optional adjuvant components (iii) may be admixed with the antidrift composition once the latter is formed in which case the resulting composition will constitute a physical mixture of the antidrift composition and adjuvant component(s) (iii). Where an optional adjuvant component (iii) is a liquid, the nature and amount of the liquid incorporated in the antidrift composition will be such that the resulting composition continues to appear as a solid.

Among the many kinds of optional adjuvant components (iii) that can be included in the antidrift composition of the invention are superspreader surfactants of both the organosilicon and non-organosilicon types and non-superspreading surfactants of both these types, one or more of which may be complexed in whole or in part with urea-based complex-forming component (i), and antifoam additives, anticaking/free flow additives, stickers, dyes, and so forth.

In a preferred embodiment of the antidrift composition herein, urea-based complex-forming component (i), in addition to being complexed with antidrift component (ii), is complexed with a superspreader surfactant. The superspreader surfactant of the preferred antidrift composition functions in an aqueous agricultural spray composition to improve the wetting and spreading of the droplets of the spray composition on the target plants.

The superspreader surfactant can be selected from among any of the known and conventional superspreader surfactants, e.g., the organosilicon superspreader surfactants disclosed in U.S. Pat. Nos. 7,507,775; 7,645,720; 7,652,072; 7,700,797; 7,879,916; and, 7,935,842, and in U.S. Patent Application Publication 2007/0131611, the entire contents of which are incorporated by reference herein, and the non-organosilicon superspreader surfactants, e.g., those disclosed in U.S. Pat. Nos. 5,821,195; 6,130,186; 6,475,953; 7,723,265; and, 7,964,552, the entire contents of which are also incorporated by reference herein.

It is within the scope of this invention to employ a mixture of organosilicon superspreader surfactant(s) and non-organosilicon superspreader surfactant(s), e.g., as disclosed in aforementioned U.S. Pat. No. 7,964,552, as optional adjuvant components (iii). Additional combinations of adjuvant surfactants that may advantageously be included in the antidrift composition of the invention include organosilicon superspreader surfactant and non-superspreading organosilicon surfactant; organosilicon superspreader surfactant and non-superspreading, non-organosilicon surfactant; non-organosilicon superspreader surfactant and non-superspreading organosilicon surfactant; non-organosilicon superspreader surfactant and non-superspreading, non-organosilicon surfactant; and, non-superspreading organosilicon surfactant and non-superspreading, non-organosilicon surfactant. The weight ratios of the different types of surfactants in these mixtures can vary widely, e.g., from 1:100 to 100:1, preferably from 1:50 to 50:1 and more preferably from 1:20 to 20:1. All, part or none of these surfactant mixtures may be complexed with urea-based complex-forming component (i) of the antidrift composition herein. Where only part of a given surfactant mixture is complexed with urea-based complex-forming component (i), the weight ratio of the different types of surfactants in the mixture may substantially correspond to, or significantly differ from, that of the mixture prior to being complexed.

More particularly, the organosilicon superspreader surfactant can be selected from any one or more of the known and conventional tri- and tetrasiloxane alkoxylate and/or hydrolysis-resistant types.

Representative of the superspreader surfactants are the polysiloxane alkoxylates of general formula (I):

$$(R^1R^2R^3SiO_{1/2})(R^4R^5SiO_{2/2})_n(R^6R^{10}SiO_{2/2})_p(R^7R^8R^9SiO_{1/2}) \quad (I)$$

wherein n is 0 or 1; p is 1 or 2; $R^1$ to $R^8$ are methyl; $R^9$ is methyl or, when $R^{10}$ is methyl, $R^9$ is $R^{11}$; $R^{10}$ is methyl or $R^{11}$ with $R^{11}$ being a polyalkylene oxide group of general formula (II):

$$R^{13}(C_2H_4O)_w(C_3H_6O)_x(C_4H_8O)_yR^{12} \quad (II)$$

in which w, x and y are independently an integer from 0 to 20, with the proviso that w is greater than or equal to 2 and w+x+y is in a range of from 2 to 20;, $R^{12}$ is a hydrogen atom, an aliphatic radical or an acetyl group; and, $R^{13}$ is a divalent aliphatic radical having the structure (III):

$$—CH_2CH(R^{14})(R^{15})_zO— \quad (III)$$

in which $R^{14}$ is a hydrogen atom or an aliphatic radical, $R^{15}$ is a divalent aliphatic radical of 1 to 6 carbon atoms and z is 0 or 1.

Especially advantageous polysiloxane alkoxylates (I) for providing optional superspreader surfactant of the antidrift composition herein are the trisiloxane alkoxylates, e.g., trisiloxane ethoxylates, trisiloxane ethoxylate-propoxylates, etc.

Polysiloxane alkoxylates (I) can be prepared in a known manner, specifically, by the hydrosilylation reaction of a silicon hydride-containing organosiloxane with an unsaturated polyalkylene oxide.

A number of polysiloxane alkoxylates (I) are commercially available such as Silwet L-77, Silwet 408, Silwet 806, SF1188A and SF1288, all from Momentive Performance Materials Inc.

Representative of the hydrolysis-resistant superspreaders are the carbosilane, disiloxane and hindered trisiloxane surfactants such as those hereinafter described.

Suitable hydrolysis-resistant carbosilane surfactants include those of general formula (IV):

$$(R^{16})(R^{17})(R^{18})Si—R^{19}—Si(R^{20})(R^{21})(R^{22}) \quad (IV)$$

wherein $R^{16}$, $R^{17}$, $R^{18}$, $R^{20}$ and $R^{21}$ are each independently selected from the group consisting of 1 to 6 monovalent hydrocarbon radicals, aryl and a hydrocarbon group of 7 to 10 carbon atoms containing an aryl group; $R^{19}$ is a divalent hydrocarbon group of 1 to 3 carbons; $R^{22}$ is a polyalkylene oxide group of general formula (V):

$$R^{23}(C_2H_4O)_d(C_3H_6O)_e(C_4H_8O)_fR^{24} \quad (V)$$

in which $R^{23}$ is a divalent linear or branched hydrocarbon radical having structure (VI):

$$—CH_2CH(R^{25})(R^{26})_gO— \quad (VI)$$

in which $R^{25}$ is hydrogen or methyl; $R^{26}$ is a divalent alkyl radical of 1 to 6 carbon atoms where the subscript g may be 0 or 1; $R^{24}$ is selected from the group consisting of hydrogen, monovalent hydrocarbon radical of 1 to 6 carbon atoms and acetyl, subject to the limitation that subscripts d, e and f are zero or positive and satisfy the following relationships:

$$2 \leq d+e+f \leq 20 \text{ with } d \geq 2.$$

Hydrolysis-resistant carbosilane surfactant (IV) can be prepared in a known manner, e.g., through the use of hydrosilylation reaction to graft an olefinically unsaturated (i.e., vinyl, allyl or methallyl) polyalkylene oxide onto a compound of the formula:

$$(R^{16})(R^{17})(R^{18})Si—R^{19}—Si(R^{20})(R^{21})H$$

wherein $R^{16}$-$R^{21}$ each has the aforedescribed meaning.

Among the suitable hydrolysis-resistant disiloxane surfactants are those of general formula (VII):

$$MM' \quad (VII)$$

wherein M is $R^{27}R^{28}R^{29}SiO_{1/2}$ and M' is $R^{30}R^{31}R^{32}SiO^{1/2}$ in which $R^{27}$ is selected from the group consisting of branched monovalent hydrocarbon radical of from 3 to 6 carbon atoms or $R^{33}$ in which $R^{33}$ is selected from the group consisting of $R^{34}R^{35}R^{36}SiR^{37}$ and $(R^{30}R^{31}R^{32})SiR^{37}$) in which $R^{34}$, $R^{35}$ and $R^{36}$ each independently is selected from the group consisting of monovalent hydrocarbon radical of from 1 to 6 carbon atoms and monovalent aryl or alkaryl hydrocarbon radical of from 6 to 13 carbon atoms and $R^{37}$ is a divalent hydrocarbon radical of from 1 to 3 carbon atoms; $R^{28}$ and $R^{29}$ each independently is selected from the group consisting of monovalent hydrocarbon radical of from 1 to 6 carbon atoms or $R^{27}$, and $R^{30}$ is a polyalkylene oxide group selected from the group consisting of $R^{38}(C_2H_4O)_a(C_3H_6O)_b(C_4H_8O)_cR^{39}$ and $R^{37}SiR^{31}R^{32}(R^{38}(C_2H_4O)_a(C_3H_6O)_b(C_4H_8O)_cR^{39})$ in which $R^{38}$ is a divalent linear or branched hydrocarbon radical having the structure (VIII):

$$—CH_2CH(R^{40})(R^{41})_dO— \quad (VIII)$$

in which $R^{40}$ is hydrogen or methyl; $R^{41}$ is a divalent alkyl radical of 1 to 6 carbon atoms in which subscript d may be 0 or 1; $R^{39}$ is selected from the group consisting of hydrogen, monovalent hydrocarbon radical of from 1 to 6 carbon atoms and acetyl subject to the limitation that subscripts a, b and c are zero or positive and satisfy the following relationships:

$$2 \leq a+b+c \leq 20 \text{ with } a \geq 2,$$

and $R^{31}$ and $R^{32}$ each independently is selected from the group of monovalent hydrocarbon radicals having from 1 to 6 carbon atoms or $R^{30}$.

Disiloxane surfactant (VII) can be prepared in a known manner, e.g., by reacting a compound of the formula $MM^H$ in which $M^H$ is the hydride precursor of the M' structural unit in disiloxane (VII) under hydrosilylation conditions with an olefinically unsaturated (i.e., vinyl, allyl or methallyl) polyalkylene oxide.

Useful hindered hydrolysis-resistant trisiloxane superspreader surfactants for complexing with complex-forming component (i) include first trisiloxane surfactant (IX), second trisiloxane surfactant (XI) and third trisiloxane surfactant (XIV) as hereinafter defined:

first hydrolysis-resistant trisiloxane of general formula (IX):

$$M^1D^1M^2 \quad (IX)$$

wherein $M^1$ is $(R^{42})(R^{43})(R^{44})SiO_{1/2}$, $M^2$ is $(R^{45})(R^{46})(R^{47})SiO_{1/2}$ and $D^1$ is $(R^{48})(Z)SiO_{2/2}$ in which $R^{42}$ is selected from a branched or linear hydrocarbon group of from 2 to 4 carbon atoms, aryl and alkyl hydrocarbon group of 4 to 9 carbon atoms containing an aryl substituent of 6 to 20 carbon atoms; $R^{43}$, $R^{44}$, $R^{45}$, $R^{46}$, $R^{47}$ and $R^{48}$ each independently is selected from the group consisting of monovalent hydrocarbon radical of 1 to 4 carbon atoms and hydrocarbon radical of 4 to 9 carbons containing an aryl group of from 6 to 20 carbon atoms, and Z is an alkyleneoxide group of general formula (X):

$$R^{49}(C_2H_4O)_a(C_3H_6O)_b(C_4H_8O)_cR^{50} \quad (X)$$

in which $R^{49}$ is a linear or branched divalent hydrocarbon radical of 2, 3, 5, 6, 7, 8 or 9 carbon atoms; $R^{50}$ is selected from the group consisting of hydrogen, monovalent hydrocarbon radicals of from 1 to 6 carbon atoms and acetyl, and in which the subscripts a, b and c are zero or positive and satisfy the following relationships:

$$2 \leq a+b+c \leq 20 \text{ with } a \geq 2;$$

second hydrolysis-resistant trisiloxane of general formula (XI):

$$M^3D^2M^4 \quad (XI)$$

wherein $M^3$ is $(R^{51})(R^{52})(R^{53})SiO_{1/2}$, $M^4$ is $(R^{54})(R^{55})(R^{56})SiO_{1/2}$ and $D^2$ is $(R^{57})(Z')SiO_{2/2}$ in which $R^{51}$, $R^{52}$, $R^{53}$, $R^{54}$, $R^{55}$, $R^{56}$ and $R^{57}$ each independently is selected from the group consisting of monovalent hydrocarbon radical of 1 to 4 carbon atoms, aryl and alkyl hydrocarbon group of 4 to 9 carbon atoms containing an aryl substituents of 6 to 20 carbon atoms; Z' is a polyalkylene oxide group of general formula (XII):

$$R^{58}(C_2H_4O)_d(C_3H_6O)_e(C_4H_8O)_fR^{59} \quad (XII)$$

in which $R^{58}$ is selected from a branched or linear divalent hydrocarbon radical of the general formula (XIII):

$$—C_4H_8O(C_2H_4O)— \quad (XIII)$$

in which $R^{59}$ is selected from the group consisting of hydrogen, monovalent hydrocarbon radical of from 1 to 6 carbon atoms and acetyl, and in which the subscripts d, e and f are zero or positive and satisfy the following relationships:

$$2 \leq d+e+f \leq 20 \text{ with } d \geq 2; \text{ and,}$$

third hydrolysis-resistant trisiloxane of general formula (XIV):

$$M^5D^3M^6 \quad (XIV)$$

wherein $M^5$ is $(R^{60})(R^{61})(R^{62})SiO_{1/2}$, $M^6$ is $(R^{63})(R^{64})(R^{65})Si_{1/2}$ and $D^3$ is $(R^{66})(Z'')SiO_{2/2}$ in which $R^{60}$, $R^{61}$, $R^{62}$, $R^{63}$, $R^{64}$ and $R^{65}$ each independently is selected from the group consisting of monovalent hydrocarbon radical of 1 to 4 carbon atoms, aryl, and alkyl hydrocarbon group of 4 to 9 carbon atoms containing an aryl substituent of 6 to 20 carbon atoms, $R^{66}$ is a linear or branched hydrocarbon radical of 2 to 4 carbons; Z" is a polyalkylene oxide group of general formula (XV):

$$R^{67}(C_2H_4O)_g(C_3H_6O)_h(C_4H_8O)_iR^{68} \quad (XV)$$

wherein $R^{67}$ is a linear or branched divalent hydrocarbon radical of 2, 3, 5, 6, 7, 8, or 9 carbon atoms; $R^{68}$ is selected from the group consisting of hydrogen, monovalent hydrocarbon radical of from 1 to 6 carbon atoms and acetyl, and in which subscripts g, h and i are zero or positive and satisfy the following relationships:

$$2 \leq g+h+i \leq 20 \text{ with } g \geq 2.$$

Hindered, hydrolysis-resistant trisiloxanes (IX), (XI) and (XII) can be prepared in a known manner, e.g., by reacting the silicone hydride precursor of one of the aforesaid trisiloxanes under hydrosilylation reaction conditions with an olefinically unsaturated (i.e., vinyl, allyl or methallyl) polyalkylene oxide.

Useful non-organosilicon superspreader surfactants include Capstone® fluorosurfactants (DuPont), and Rhodasurf® DA-530 (Rhodia).

Useful non-superspreading organosilicon surfactants include Silwet® L-8610, L-8020, L-6900, L-6988 and L-5440.

Useful non-superspreading, non-organosilicon surfactants include those of the anionic, nonionic, cationic and amphoteric varieties.

Suitable non-superspreading, non-organosilicon anionic surfactants include sodium dodecyl sulfate, alkylcarboxylic acids (Lutensit® AN 45 (BASF)), sodium fatty alcohol polyglycol ether sulfates (Emulphor® FAS 30 (BASF)), sodium laureth sulfate (Rhodapex® ESB 70 FEA2 (Rhodia)), and the like.

Suitable non-organosilicon nonionic surfactants, which depending on structure may or may not be superspreading, include nonylphenol and octylphenol ethoxylates, ethylene oxide/propylene oxide block copolymers such as the Pluronics® (BASF), fatty alcohol ethoxylates (Emulan® emulsifiers (BASF)), alcohol ethoxylates (Rhodasurf® surfactants (Rhodia)) and the like.

Where an organosilicon superspreader surfactant (iii) is present in the antidrift composition, it can be especially advantageous to include a non-organosilicon nonionic surfactant of general formula (XVI):

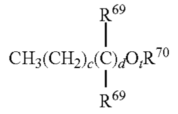

(XVI)

wherein $R^{69}$ is the same or different and is selected from the group consisting of hydrogen and an alkyl of 1 to 4 carbon atoms; c is 5 to 9, d is 0 to 4, c+d is 5 to 9 and t is 0 or 1; $R^{70}$ is a nonionic hydrophilic moiety with the proviso that when t is 0, $R^{70}$ is

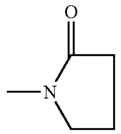

and when t is 1, $R^{70}$ is selected from the group consisting of (i) $[C_2H_4O]_f[C_3H_6O]_gH$ and (ii) $(C_6H_9O_5)_h—C_6H_{10}O_5$ in which f is 1 to 40, g is 0 to 40 and h is 1 to 4, all as disclosed in U.S. Pat. No. 5,558,806, the entire contents of which are incorporated by reference herein. Combinations of organosilicon-containing superspreader surfactant (iii) and nonionic cosurfactant (XVI) that can advantageously be incorporated in the antidrift composition herein include the products Agrospred 100 and Agrospred 730, both available from Momentive Performance Materials Inc.

Suitable non-organosilicon cationic surfactants include tallow amine ethoxylates, trimethylalkylammonium chloride, and the like.

Suitable non-organosilicon amphoteric surfactants include the sulfobetaines and cocamidobetaines, all of which are able to be complexed with urea-based complex-forming component (i).

Specific antifoam additives include silicone oils, silica/silicone oil blends, silicone resins, alkoxylated cloud-point antifoams, and the like; specific anticaking/free-flow additives include silica, calcium silicate, sodium silicate, tricalcium phosphate, bentonite, aluminum silicate, magnesium trisilicate, and the like; and, specific stickers include latexes, and the like.

Where utilized, these and other optional adjuvant components (iii) can be incorporated in the antidrift composition of the invention in known and conventional amounts.

4. Optional Formulation Component (iv)

It is also within the scope of the invention to provide the antidrift composition herein as a semi-wet paste or even as a fully dissolved or dispersed liquid concentrate in which case any added water, organic solvent, etc., employed in providing the antidrift composition in one of these forms can be considered an optional formulation component (iv).

5. Ranges of Amounts of Components (i), (ii), and Optional Adjuvant Component (iii) in the Antidrift Composition Provided that urea-based complex-forming component (i) is present in the antidrift composition of the invention in at least an amount that is effective to form a complex with significant amounts of antidrift component (ii), e.g., at least 50, preferably at least 80, and more preferably at least 95, weight percent of antidrift component (ii), and antidrift component (ii) is present in the antidrift composition in at least an amount that is effective to provide appreciable drift control of the aqueous spray composition to which the antidrift composition is added, components (i) and (ii) of the antidrift composition can be present therein within broadly specific amounts.

Thus, e.g., the antidrift composition of the invention can contain an amount of complex-forming component (i), antidrift component (ii) and optional adjuvant component (iii), within one of the weight parts ranges A, B and C as hereinafter set forth (with weight parts values for a particular antidrift composition totaling 100 weight percent):

| Component of the Antidrift | Weight Parts Ranges A, B and C | | |
|---|---|---|---|
| Composition | A | B | C |
| (i) | 55-99.9 | 70-95 | 80-98 |
| (ii) | 0.1-25 | 0.5-10 | 1-5 |
| (iii) | 0-20 | 1-20 | 1-15 |

6. General Preparative Procedures

The antidrift composition of the invention can be readily prepared by a variety of procedures. Thus, e.g., the desired amounts of antidrift component (ii) and, if utilized, optional adjuvant component (iii), can be dissolved in an aqueous and/or organic solvent solution of the desired amount of urea-based complex-forming component (i) followed by removal of the water/organic solvent to provide a substantially solid material which, if desired, can be pulverized, granulated, flaked, pelletized, prilled or otherwise processed to provide suitably convenient end-user forms for addition to aqueous spray media. Organic solvents suitable for this purpose include low boiling polar solvents such as methanol, ethanol, propanol, isopropanol, acetone, methylethylketone, dimethylformamide, dimethylsulfoxide, and the like. Removal of solvent can be accelerated by application of suitable levels of heat and/or reduced pressure. Drying can be accomplished employing any of several known and conventional techniques for removing solvent(s) from dissolved solids, e.g., natural air drying, oven drying, drum drying, spray drying, evaporative drying under ambient or reduced pressure, supercritical drying, etc.

Where such drying techniques result in a bulk solid or fairly large lumps of solid material, it is generally desirable to grind, mill or otherwise reduce the dry material to some particulate form, e.g., powder, granules, flakes, pellets, prills, etc., in order to facilitate packaging and/or handling by end-users. Whether the particulates are produced by grinding/milling the dried material or are produced directly from a solution or melt by such techniques as spray drying, prilling, and the like, the particulates can range widely as to both average particle size and particle size distribution. Antidrift compositions having average particle sizes of from 50μ to 10 mm, and preferably from 200μ to 5 mm, and in which from 50 to 70, and preferably from 60 to 90, weight percent of the compositions are made up of particles having average sizes of from 400μ to 1 mm, are generally quite suitable forms of the compositions herein.

In accordance with another procedure for producing the antidrift composition of the invention, the desired amounts of antidrift component (ii) and, optionally, adjuvant component (ii), can be uniformly dissolved in the desired amount of molten urea-based complex-forming component (i) (in the case of essentially pure or technical grade urea, at or above its melting point of 133-135° C.) and following cooling and solidification of the mixture, further processing of the mixture, e.g., grinding or milling to provide powder, as previously indicated. To accelerate dissolution of antidrift component (ii) and any optional adjuvant component (iii) into the molten urea-based complex-forming component (i), a minor amount of water, e.g., up to 30% by weight, may be added to complex-forming component (i) prior to heating the resulting mixture to its (reduced) melt temperature.

B. Aqueous Spray Compositions Containing the Antidrift Composition of the Invention The antidrift composition of the present invention is especially useful for addition to aqueous spray compositions intended for agricultural (inclusive of horticultural, turf and/or forestry) application. The amounts of antidrift composition to be added to a given aqueous spray composition will, of course, be that which is effective to significantly reduce drift of that particular spray composition.

Determining the effective range of amounts of antidrift composition for a given aqueous spray composition will be influenced by a variety of factors including the precise formulation of the antidrift composition, the desired distribution of droplet sizes for the spray composition under consideration, the spray conditions and the nature of the target plants/crops/vegetation.

Optimum amounts of antidrift composition for a specific spray composition and spraying operation can be readily determined employing routine experimental testing procedures such as those described below.

For many spray compositions, amounts of antidrift composition of this invention ranging from 0.01 to 5, and preferably from 0.1 to 1, weight percent can be incorporated therein with generally good drift reduction results.

Agricultural sprays, which in addition to water and the water-soluble antidrift composition of the invention, will include one or more known and conventional active ingredients, fertilizers, micronutrients, adjuvants, agricultural excipients, cosurfactants, etc., such as those now described.

1. Pesticides

Pesticidal sprays include at least one pesticide. Optionally, the pesticidal spray may include excipients, cosurfactants, solvents, foam control agents, deposition aids, biologicals, micronutrients, fertilizers, and the like. The term "pesticide" means any compound that is used to destroy pests, e.g., rodenticides, insecticides, miticides, acaricides, fungicides, herbicides, and so forth. Illustrative examples of pesticides that can be employed include, but are not limited to, growth regulators, photosynthesis inhibitors, pigment inhibitors, mitotic disrupters, lipid biosynthesis inhibitors, cell wall inhibitors, and cell membrane disrupters. The amount of pesticide employed in a spray composition will vary with the particular type of pesticide. Specific examples of pesticide compounds that can be incorporated in a spray composition include, but not limited to, herbicides and growth regulators such as: phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, sulfonylureas, imidazolinones, clethodim, diclofop-methyl, fenoxaprop-ethyl, fluazifop-p-butyl, haloxyfop-methyl, quizalofop, sethoxydim, dichlobenil, isoxaben, bipyridylium compounds, and the like.

Fungicide compositions that can be utilized in the aqueous spray composition include, but are not limited to, aldimorph, tridemorph, dodemorph, dimethomorph; flusilazol, azaconazole, cyproconazole, epoxiconazole, furconazole, propiconazole, tebuconazole and the like; imazalil, thiophanate, benomyl carbendazim, chlorothialonil, dicloran, trifloxystrobin, fluoxystrobin, dimoxystrobin, azoxystrobin, furcaranil, prochloraz, flusulfamide, famoxadone, captan, maneb, mancozeb, dodicin, dodine, metalaxyl, and the like.

Insecticide, larvacide, miticide and ovacide compounds that can incorporated in the aqueous spray composition include, but are not limited to, *Bacillus thuringiensis* (or Bt), spinosad, abamectin, doramectin, lepimectin, pyrethrins, carbaryl, primicarb, aldicarb, methomyl, amitraz, boric acid, chlordimeform, novaluron, bistrifluoron, triflumuron, diflubenzuron, imidacloprid, diazinon, acephate, endosulfan, kelevan, dimethoate, azinphos-ethyl, azinphos-methyl, izoxathion, chlorpyrifos, clofentezine, lambda-cyhalothrin, permethrin, bifenthrin, cypermethrinrn, and the like.

2. Fertilizers and Micronutrients

Fertilizers and micronutrients include, but not limited to, zinc sulfate, ferrous sulfate, ammonium sulfate, urea, urea ammonium nitrogen, ammonium thiosulfate, potassium sulfate, monoammonium phosphate, urea phosphate, calcium nitrate, boric acid, potassium and sodium salts of boric acid, phosphoric acid, magnesium hydroxide, manganese carbonate, calcium polysulfide, copper sulfate, manganese sulfate, iron sulfate, calcium sulfate, sodium molybdate, calcium chloride, and the like.

3. Adjuvants and Agricultural Excipients

Many pesticide applications require the addition of an adjuvant to the aqueous spray formulation to provide wetting and spreading on foliar surfaces. Often that adjuvant is a surfactant that is capable of performing several functions such as increasing spray droplet retention on difficult to wet leaf surfaces, enhancing spreading to improve spray coverage and providing penetration of herbicide into the plant cuticle.

Buffers, preservatives and other standard agricultural excipients known in the art may also be included in the spray composition.

Suitable organic solvents for inclusion in the spray composition include alcohols, aromatic solvents, oils (e.g., mineral oil, vegetable oil, silicone oil, and so forth), lower alkyl esters of vegetable oils, fatty acids, ketones, glycols, polyethylene glycols, diols, paraffinics, and so forth. Particular solvents include 2,2, 4-trimethyl, 1-3-pentane diol and alkoxylated (especially ethoxylated) versions thereof as illustrated in U.S. Pat. No. 5,674,832, the entire contents of which are incorporated by reference herein, and n-methyl-pyrrolidone.

4. Cosurfactants

Useful cosurfactants herein include nonionic, cationic, anionic, amphoteric and zwitterionic surfactants and any of their mixtures. Surfactants are typically hydrocarbon-based, silicone-based or fluorocarbon-based.

Moreover, other cosurfactants having short chain hydrophobes that do not interfere with superspreading, e.g., those described in U.S. Pat. No. 5,558,806, the entire contents of which are incorporated by reference herein, are also useful.

Useful surfactants include alkoxylates, especially ethoxylates, containing block copolymers including copolymers of ethylene oxide, propylene oxide, butylene oxide, and mixtures thereof; alkylarylalkoxylates, especially ethoxylates or propoxylates and their derivatives including alkyl phenol ethoxylate; arylarylalkoxylates, especially ethoxylates or propoxylates. and their derivatives; amine alkoxylates, especially amine ethoxylates; fatty acid alkoxylates; fatty alcohol alkoxylates; alkyl sulfonates; alkyl benzene and alkyl naphthalene sulfonates; sulfated fatty alcohols, amines or acid amides; acid esters of sodium isethionate; esters of sodium sulfosuccinate; sulfated or sulfonated fatty acid esters; petroleum sulfonates; N-acyl sarcosinates; alkyl polyglycosides; alkyl ethoxylated amines, and the like.

Specific examples include alkyl acetylenic diols (Surfynols®, Air Products), pyrrilodone based surfactants (e.g., Surfadone® LP 100, Ashland), 2-ethyl hexyl sulfate, isodecyl alcohol ethoxylates (e.g., Rhodasurf® DA 530, Rhodia), ethylene diamine alkoxylates (Tetronics®, BASF), ethylene oxide/propylene oxide copolymers (Pluronics®, BASF), gemini-type surfactants (Rhodia) and diphenyl ether gemini-type surfactants (DOWFAX®, Dow Chemical).

Preferred surfactants include ethylene oxide/propylene oxide copolymers (EO/PO); amine ethoxylates (tallowamine ethoxylates); alkyl polyglycosides; oxo-tridecyl alcohol ethoxylates, and so forth.

5. Other Aqueous Spray Components

The aqueous spray composition can include one or more other agrochemical components. Suitable such agrochemical components are growth regulators, biologicals, plant nutritionals, paraffinic mineral oil, methylated seed oils (i.e. methylsoyate or methylcanolate), vegetable oils (such as soybean oil and canola oil), water conditioning agents such as Choice® (Loveland Industries, Greeley, Colo.) and Quest (Helena Chemical, Collierville, Term.), modified clays such as Surround® (Englehard Corp.,), foam control agents, wetting agents, dispersants, emulsifiers and deposition aids.

Agricultural spray compositions may be made by combining in any combination and/or sequence in a manner known in the art, such as mixing, water, one or more of the above spray components and the antidrift composition of the present invention, either as a tank-mix, or as an "In-can" formulation. The term "tank-mix" means the addition of at least one agrochemical to a spray medium, such as water or oil, at the point of use. The term "In-can" refers to a formulation or concentrate containing at least one agrochemical component. The "In-can" formulation may then be diluted to its application concentration at the point of use, typically in a tank-mix, or it may be used undiluted.

C. Examples Illustrating the Antidrift Composition of the Invention

1. Determination of Spray Drift

Spray drift was determined in the examples that follow employing the spray booth apparatus of FIG. 1 that has been modified to function in the manner of a small wind tunnel. A flat-fan spray nozzle (UNIJET 8002E) was fixed in place at the top of the booth, about 56 cm from the right hand side of the hood. A heat gun in "fan mode" was used as a wind source and placed to the right of the spray. A water sensitive paper coupon was held on the opposite side of the spray. This setup is shown in FIG. 1. The spray drift tests were run at a spray pressure of 2.85-3.00 atm and the spray time was 10 seconds. Three to four sprays were run for each solution. The amount of drift was determined by averaging the number of drops counted in five 0.125 $cm^2$ circles on each water sensitive paper coupon. The coupons measured approximately 1.8×2.5 cm. Water was sprayed as a control at the beginning and end of each set.

2. Determination of Spreading/Wetting

The spreading ability of the various superspreaders utilized herein was determined by depositing a single drop (10 microliters) of solution onto a clean, flat polystyrene dish. The polystyrene surfaces were cleaned by rinsing with isopropanol and then with deionized water. The dishes were then dried with dry nitrogen gas. The diameters of the resulting drops were then measured. Each solution was tested 2 to 4 times and the average diameter was calculated.

EXAMPLES 1-10

In these and all of the other examples that follow, all percentage amounts of indicated materials are by weight.

Spray drift and spreading tests were carried out on a mechanical mixture of a polyacrylamide (PAM) antidrift agent (Zetag 1100, BASF) and a complex of urea and a hydrolysis-resistant carbosilane superspreader surfactant ("Silicone A") (Example 2) made by adding the superspreader surfactant to molten urea. The results of these tests, presented in Table 1 below, show that this mixture exhibits a level of drift reduction that is substantially equivalent to that exhibited by a similar concentration of PAM antidrift agent (Example 7) and wetting/spreading properties that are significantly better than deionized water (Examples 1 and 8) despite the low concentration of Silicone A.

TABLE 1

Spray Drift and Spreading Test Results Data for Various Urea Complexes
Aqueous Spray Composition

| Example | Test Sample Description | % Sample Evaluated | % Urea | % Silicone A | % PAM | Average Spray Drift {drops/ 0.125 $cm^2$) | St Dev (drops/ 0.125 $cm^2$) | Average Diameter (mm) | St Dev {mm) |
|---|---|---|---|---|---|---|---|---|---|
| 1 | DI water | | 0.000 | 0.000 | 0.000 | 25.7 | 3.3 | 4.8 | 0.5 |
| 2 | mechanical blend of 97% urea complex (containing 7.6% Silicone A) and 3% PAM | 0.33 | 0.296 | 0.024 | 0.010 | 3.7 | 1.6 | 10.3 | 1.4 |
| 3 | urea complex containing 1.2% PAM and 4.0% Silicone A and made from aq. soln of these components | 0.833 | 0.790 | 0.033 | 0.010 | 2.4 | 0.5 | 25.3 | 2.9 |
| 4 | urea complex containing 2.3% PAM and 7.74% Silicone A and made from aq. soln of these components | 0.435 | 0.391 | 0.033 | 0.010 | 5.2 | 2.1 | 23.3 | 6.5 |
| 5 | urea complex containing 2.3% PAM and 7.74% Silicone A and made from aq. soln of these components | 0.904 | 0.813 | 0.070 | 0.021 | 2.6 | 1.0 | 30.9 | 8.1 |
| 6 | urea complex containing 1.96% PAM made from molten urea | 0.51 | 0.500 | 0.000 | 0.010 | 5.1 | 1.1 | 5.2 | 0.5 |
| 7 | PAM | 0.01 | 0.000 | 0.000 | 0.010 | 3.0 | 1.1 | 5.2 | 0.4 |
| 8 | DI water (repeat) | | 0.000 | 0.000 | 0.000 | 20.5 | 2.1 | 4.8 | 0.5 |
| 9 | Silicone A | 0.033 | 0.000 | 0.033 | 0.000 | | | 15.5 | 2.9 |
| 10 | Silicone A | 0.07 | 0.000 | 0.070 | 0.000 | | | 23.3 | 2.2 |

While the mechanical mixture of urea/Silicone A superspreader complex and PAM (Example 2) yields a free-flowing particulate product providing excellent drift control and good spreading properties, it does not address the problem of the characteristically slow dissolution of the PAM antidrift agent. In addition there is a concern that the two kinds of particulates in the mixture, i.e., urea/Silicone A complex and PAM, will separate from each other to some extent during storage thereby resulting in a heterogenous mixture that may complicate achieving the required proportioning when preparing the aqueous spray composition.

In Example 6, and in accordance with the invention, the PAM antidrift component was dissolved within the molten urea to complex the PAM. This liquid mixture was then cast onto a room temperature aluminum dish to form a brittle solid. This solid inclusion complex was then broken up and ground to form a white, free-flowing powder.

Urea inclusion complexes containing both the antidrift agent and superspreader surfactant were prepared by dissolving the superspreader, antidrift agent and urea in water in the desired ratio. The water was then removed by evaporation by placing the solution in an oven at 80-95° C. for 2-3 days resulting in white and semi-crystalline solids. When ground, the resulting antidrift compositions were white, free-flowing powders (Examples 3-5).

When diluted to achieve a superspreader concentration of 0.033% and a PAM concentration of 0.01% (Examples 3 and 4), these inclusion complexes reduced spray drift as well as the control solution of 0.01% PAM (Example 7). Surprisingly, the urea inclusion complexes of Examples 3 and 4 also exhibited better spreading than the 0.033% control solution of Silicone A superspreader (Example 9). The urea/PAM/Silicone A superspreader inclusion complex of Example 4 was also evaluated at approximately twice the initial concentration resulting in a PAM concentration of 0.021% and a superspreader concentration of 0.070% (Example 5). This complex exhibited excellent drift reduction and better spreading/wetting than the more dilute complex solutions of Examples 3 and 4. The complex of Example 5 also showed better spreading/wetting that the 0.070% control solution of Silicone A superspreader (Example 10). Example 6, a urea inclusion complex of PAM with no superspreader Silicone A, showed excellent drift reduction but very poor spreading properties comparable to those observed with water thus demonstrating that urea by itself does not improve spreading/wetting properties.

EXAMPLES 11-21

Another set of urea/PAM/Silicone A superspreader inclusion complexes were prepared as indicated in Table 2 below. The complexes of Examples 12-15 were made via the aqueous solution procedure described above in order to determine how much Silicone A superspreader and PAM could be incorporated in the inclusion complex. Examples 16 and 18 were made with polycrylamide-polyacrylic acid (PAM-PAA) copolymer having a nominal weight average molecular weight of 15,000 (Aldrich) as the antidrift agent instead of PAM. Example 16, like Examples 12-15, was made via the aqueous solution procedure. Examples 17 and 18 were prepared from molten urea with PAM and PAM-PAA copolymer, respectively. All of these complexes were sprayed at a dilution providing an antidrift component concentration of 0.015%. At these dilutions, the Silicone A concentration of Examples 12-16 was 0.050% while those of Examples 17 and 18 was 0.041%. The results of spray-drift and spreading/wetting tests are summarized in Table 2 below.

TABLE 2

Spray Drift and Spreading Test Results for Various Urea Complexes

| | | Spray Composition | | | | | | | |
|---|---|---|---|---|---|---|---|---|---|
| Example | Test Sample Description | % Test Sample Evaluated | % Urea | % Silicone A | % PAM or PAM-PAA | Average Spray Drift (drops/ 0.125 $cm^2$) | St Dev {drops/ 0.125 $cm^2$) | Average Diameter (mm) | St Dev (mm) |
| 11 | DI water | | | | | 41.4 | 5.4 | 4.5 | 0.6 |
| 12 | urea complex containing 1.20% PAM and 4.03% Silicone A made from aq. soln of components | 1.246 | 1.18 | 0.050 | 0.015 | | | | |
| 13 | urea complex containing 2.31% PAM and 7.67% Silicone A made from aq. soln of components | 0.649 | 0.58 | 0.050 | 0.015 | 4.1 | 0.9 | 34.1 | 2.5 |
| 14 | urea complex containing 3.00% PAM and 10.02% Silicone A made from aq. soln of components | 0.500 | 0.44 | 0.050 | 0.015 | 6.5 | 3.1 | 31.3 | 2.2 |
| 15 | urea complex containing 3.99% PAM and 13.31% Silicone A made from aq. soln of components | 0.376 | 0.31 | 0.050 | 0.015 | 3.7 | 1.2 | 31.0 | 3.6 |
| 16 | urea complex containing 2.31% PAM/PAA (Aldrich) and 7.67% Silicone A made from aq. soln of components | 0.649 | 0.58 | 0.050 | 0.015 | 4.7 | 1.3 | 31.3 | 3.3 |
| 17 | urea complex containing 2.0% PAM and 5.5% Silicone A made from molten urea | 0.750 | 0.69 | 0.041 | 0.015 | 4.7 | 0.5 | 22.3 | 4.3 |
| 18 | urea complex containing 2.0% PAM/PAA (Aldrich) and 5.5% Silicone A made from molten urea | 0.750 | 0.69 | 0.041 | 0.015 | 2.0 | 0.0 | 27.0 | 6.7 |
| 19 | PAM | 0.015 | 0.00 | 0.000 | 0.015 | 3.1 | 1.0 | 4.5 | 0.6 |
| 20 | Silicone A | 0.05 | 0.00 | 0.050 | 0.000 | 42.7 | 6.3 | 20.0 | 7.6 |
| 21 | DI water | | | | | 39.7 | 3.4 | | |

As shown in the Table 2 data, all of the urea/antidrift agent/Silicone A superspreader inclusion complexes (Examples 12-18) provided levels of spray-drift reduction essentially equivalent to that of the PAM control (Example 19). In addition, these inclusion complexes provided better spreading/wetting properties than the equivalent concentration of Silicone A superspreader in water (Example 20).

Polyacrylamides such as Zetag 1100 (BASF) currently do not have EPA "inert" status under Title 40, Code of Federal Regulations Sec. 180.960. However PAM/PAA copolymers with average molecular weights in atomic mass units (amu) equal to or greater than 1200, and PAM/PAA/Na polymers (CAS#25085-02-3) with a number average molecular weight (amu) of at least 18,000, are considered "inert" under this regulation and are thus acceptable for use in agricultural sprays.

EXAMPLES 22-29

Urea inclusion complexes containing PAM-PAA copolymer, sodium salt (PAM-PAA-Na) (Zetag 4100, BASF), both without and with Silicone A superspreader, were made from molten urea as was a comparison urea inclusion complex containing PAM and Silicone A. Aqueous herbicidal spray compositions were prepared containing 0.75% of these urea inclusion complexes and 1% glyphosate isopropylamine salt ("glyphosate WA salt") herbicide and evaluated for reduction of drift, increased spreading and herbicidal performance when sprayed on velvetleaf. The results of these tests are summarized in Table 3 below.

TABLE 3

Spray Drift and Spreading Data for Various Urea Complexes
Aqueous Herbicidal Spray Composition

| Example | Test Sample Description | % Glyphosate | % Test Sample Evaluated | % Urea | % Silicone A | % PAM or PAM-PAA-Na | Average Spray Drift (drops/ 0.125 $cm^2$) | Drop Spread Diameter (mm) | % Control after 1 week | % Control after 2 weeks |
|---|---|---|---|---|---|---|---|---|---|---|
| 22 | DI water | 0.0 | 0 | 0 | 0 | 0 | 34.1 | | | |
| 23 | urea complex containing 2.0% PAM and 5.5% Silicone A | 1 | 0.750 | 0.69 | 0.041 | 0.015 | 8.7 | 20.5 | 48 | 91 |
| 24 | urea complex containing 1.0% PAM-PAA-Na and no Silicone A | 1 | 0.750 | 0.74 | 0 | 0.0075 | 7.7 | 5.3 | 43 | 90 |
| 25 | urea complex containing 1.0% PAM-PAA-Na and 5.0% Silicone A | 1 | 0.750 | 0.71 | 0.038 | 0.0075 | 11.5 | 17.3 | 43 | 93 |
| 26 | Silicone A | 1 | 0.042 | 0 | 0.042 | 0 | 23.7 | 21.5 | 30 | 94 |
| 27 | glyphosate IPA salt | 1 | 0 | 0 | 0 | 0 | 33.5 | 4.8 | 25 | 81 |
| 28 | water/no spray control | 0 | 0 | 0 | 0 | 0 | 44.1 | 3.8 | 0 | 0 |
| 29 | Silicone A | 0 | 0.042 | 0 | 0.042 | 0 | | 21.8 | | |

As shown in the data of Table 3, the greatest reduction in drift was achieved with urea/PAM-PAA-Na complex containing no Silicone A superspreader (Example 24). The addition of Silicone A superspreader to the urea/PAM-PAA-Na inclusion complex of Example 25 resulted in a slight increase in drift. While the urea/PAM/Silicone A inclusion complex of Example 23 resulted in slightly better drift reduction than the urea/PAM-PAA-Na/Silicone A complex of Example 25, twice as much PAM was required to achieve this result.

Drop-spreading tests showed that solutions containing Silicone A superspreader resulted in average drop spread diameters of approximately 20 mm regardless of whether or not they had been part of a urea inclusion complex and regardless of whether or not glyphosate herbicide was present. The compositions that did not contain Silicone A superspreader did not spread well, with resulting drop diameters being about 5 mm.

The three herbicidal compositions containing urea inclusion complexes (Examples 23-25) were sprayed on velvetleaf. A solution of 0.042% Silicone A and 1% glyphosate IPA salt (Example 26) was used as a control as was a plain 1% glyphosate IPA salt solution (Example 27). After one week the three herbicidal compositions containing the urea inclusion complexes and glyphosate IPA salt (Examples 23-25) were more effective at killing the velvetleaf than the Silicone A and glyphosate IPA salt control (Example 26) which was slightly more effective that the 1% glyphosate control (Example 27). After two weeks, the three urea inclusion complexes and the silicon A/glyphosate IPA salt combination (Examples 23-26) all exhibited greater than 90% herbicidal effectiveness while the glyphosate IPA salt control provided only 81% herbicidal effectiveness.

EXAMPLES 30-38

Larger batches of urea inclusion complexes containing PAM-PAA-Na antidrift agent and Silicone A superspreader were prepared in order to identify any possible problems that might result when scaling up from 40-50 g to 120-150 g batch quantities. The three inclusion complexes all contained 5% Silicone A superspreader and different concentrations of PAM-PAA-Na antidrift component. Aqueous spray compositions containing 0.75% of each of these inclusion complexes were then prepared and tested for spray drift control and spreading/wetting properties. The results of these studies are presented in Table 4 below.

TABLE 4

Spray Drift and Spreading Test Results Data for Complexes and
Mixtures of Urea and PAM-PAA-Na Copolymer Antidrift Agent
Aqueous Spray Composition

| Example | Test Sample Description | % Sample Evaluated | % Urea | % Silicone A | % Antidrift Agent | Average Spray Drift (drops/0.125 cm2) | St Dev (drops/ 0.125 cm2) | Average Spread Diameter (mm) |
|---|---|---|---|---|---|---|---|---|
| 30 | DI water | | | | | 24.6 | 6.3 | 5.0 |
| 31 | urea complex containing 1% PAM-PAA-Na and 5% Silicone A | 0.75 | 0.705 | 0.0375 | 0.0075 | 5.0 | 2.4 | 23.5 |
| 32 | urea complex containing 1.33% PAM-PAA-Na and 5% Silicone A | 0.75 | 0.703 | 0.0375 | 0.0100 | 4.3 | 1.8 | 24.0 |

TABLE 4-continued

Spray Drift and Spreading Test Results Data for Complexes and Mixtures of Urea and PAM-PAA-Na Copolymer Antidrift Agent
Aqueous Spray Composition

| Example | Test Sample Description | % Sample Evaluated | % Urea | % Silicone A | % Antidrift Agent | Average Spray Drift (drops/0.125 cm2) | St Dev (drops/ 0.125 cm2) | Average Spread Diameter (mm) |
|---|---|---|---|---|---|---|---|---|
| 33 | urea complex containing 0.67% PAM-PAA-Na and 5% Silicone A | 0.75 | 0.707 | 0.0375 | 0.0050 | 5.3 | 0.3 | 29.5 |
| 34 | PAM-PAA copolymer | | 0 | 0 | 0.0075 | 5.9 | 0.7 | 5.3 |
| 35 | mechanical mixture of urea and PAM-PAA-Na | | 0.705 | 0 | 0.0075 | 5.5 | 2.4 | 5.5 |
| 36 | Silicone A | | 0 | 0.0375 | 0 | 25.7 | 4.0 | 22.3 |
| 37 | mechanical mixture of urea and Silicone A | | 0.705 | 0.0375 | 0 | 20.4 | 4.2 | 23.3 |
| 38 | DI water | | | | | 24.9 | 5.8 | |

As observed with the smaller scale lots, the inclusion complexes of Table 4 (Examples 31-33) exhibited good drift control that was equivalent to that provided by the control samples of PAM-PAA-Na with and without urea (Examples 34 and 35). The urea inclusion complexes also exhibited spreading/wetting properties that were as good as or better that that obtained with the aqueous Silicone A solution (Example 36). The solution of Silicone A with urea (Example 37) spread a little better than the Silicone A solution (Example 36). The inclusion complexes of Examples 31 and 32 resulted in drop diameters that were a little better than the Silicone A solution. The inclusion complex of Exhibit 33 demonstrated significantly better spreading/wetting properties than the silicone superspreader solution of Example 36.

EXAMPLES 39-47

The effect of complexing the antidrift agent in urea on the dissolution time of the antidrift agent was also evaluated. Full dissolution was considered to have been achieved when a solution appeared clear and was lump-free when poured. The results of these dissolution studies are presented in Tables 5 and 6 as follows:

TABLE 5

Dissolution Time for Various PAM-PAA-Na Compositions

| Example | Test Sample Description | Particle Size (diameter) Range (μ) | % Sample Dissolved | Solvent | Final PAM-PAA-Na % Concentration | Final Urea % Concentration | Dissolution Time (min) |
|---|---|---|---|---|---|---|---|
| 39 | flaked urea/PAM-PAA-Na complex (1.5% Pam in 98.5% urea) | 650-7500 | 0.67 | DI water | 0.01 | 0.66 | 4.5 |
| 40 | gound urea/PAM-PAA-Na complex (1.5% Pam in 98.5% urea) | 160-560 | 0.67 | DI water | 0.01 | 0.66 | 2 |
| 41 | PAM-PAA-Na | 400-1100 | 0.01 | 1% urea in DI water | 0.01 | 1.00 | 185 |
| 42 | PAM-PAA-Na | 400-1100 | 0.01 | 0.67% urea in DI water | 0.01 | 0.66 | 200 |
| 43 | PAM-PAA-Na | 400-1100 | 0.01 | DI water | 0.01 | 0.00 | 245 |

As the dissolution data in Table 5 show, both the flaked and ground antidrift composition of the invention (Examples 39 and 40) dissolved in less than 5 minutes whereas the PAM-PAA-Na copolymer required 185-200 minutes to dissolve in the aqueous urea solutions (Examples 41 and 42) and 245 minutes to dissolve in water (Example 43).

TABLE 6

Dissolution Times for Various PAM-PAA-Na Compositions

| Example | Test Sample Description | % Urea | % PAM-PAA-Na Copolymer | % Silicone A | Dissolution Time (min) |
|---|---|---|---|---|---|
| 44 | 1% urea complex (94% urea, 1% PAM-PAA-Na and 5% Silicone A) | 0.940 | 0.010 | 0.050 | 9 |
| 45 | solution equivalent to Sample 1 | 0.940 | 0.010 | 0.050 | 135 |
| 46 | PAM-PAA-Na | | 0.010 | | 690 |
| 47 | urea and PAM-PAA-Na | 0.940 | 0.010 | | 90 |

As the dissolution data in Table 6 show, Example 44, a 1% solution of urea inclusion complex (94% urea, 1% PAM-PAA-Na and 5% Silicone A) required 9 minutes of continuous rolling to fully dissolve. Example 45 was prepared by sequentially dissolving the individual components of Example 44. The urea, a fine powder, and Silicone A, a liquid, were added first. These ingredients went into solution very quickly. The PAM-PAA-Na, a fine, granular solid, was then added. The PAM-PAA-Na required 135 minutes to fully dissolve. Example 46, PAM-PAA-Na by itself, required 690 minutes to fully go into solution. However, when mixed with urea in Example 47, the PAM-PAA-Na dissolved in just 90 minutes. It is clear from these dissolution studies that the presence of urea accelerates the solubilization of PAM-PAA-Na. It is also evident that the PAM-PAA-Na component of the urea/PAM-PAA-Na/Silicone A inclusion complex dissolves much faster than the equivalent amount of non-complexed PAM-PAA-Na in a urea solution.

EXAMPLES 48-57

These examples illustrate antidrift compositions of the invention containing a conventional trisiloxane superspreader surfactant ("Silicone B").

Two urea complexes were prepared, one in the absence of water ("dry preparation") and one to which water was added ("wet preparation"). For both preparations, 94 g urea, 1 g PAM-PAA-Na antidrift component and 5 g Silicone B superspreader component were added to a flask. In the case of the wet preparation, 10 g DI water were also added to its flask. Each flask was then attached to a Rotovap and a nitrogen blanket was applied. The flasks were partially submerged in an oil bath set at 150° C. and rotated at approximately 100 rpm until the urea melted and the PAM-PAA-Na and Silicone B components dissolved therein.

Dissolution times (min) for the dry- and wet-prepared urea/PAM-PAA-Na/Silicone B complexes and spreading test results are presented in Table 7 below:

The spreading data in Table 7 show that the urea complexes of Examples 49 and 50 spread just as well as the equivalent concentration of Silicone B superspreader in the control (Example 51) demonstrating that the wetting properties of Silicone B are not adversely affected by either the urea complex-forming component or the PAM-PAA-Na antidrift component and that the Silicone B does not undergo significant hydrolysis either during the synthesis of the urea/PAM-APP-Na/Silicone B complex or during 5 weeks of storage.

As the dissolution data in Table 7 show, the addition of water to the mixture providing the wet urea complex of Example 50 resulted in a dissolution time of 25 minutes in contrast to the dissolution time of 45 minutes for the dry urea complex of Example 49. While the wet urea complex of Example 50 contains some small amount of water, when ground the resulting product exhibited some degree of flowability. Removal of some or all of this water to provide an essentially water-free complex, e.g., one comparable in appearance and flow to the dry urea complex of Example 49, may be carried out to improve the processability of the wet urea complex of Example 50.

The spray-drift test results for the dry- and wet-prepared urea complexes of Examples 49 and 50 of Table 7 are presented in Table 8 below:

TABLE 7

Urea Complex Dissolution Times and Spreading Results after 1 and 5 Weeks Storage of Spreading Solution

| Example | Description | Dissolution Time at 150 C. Bath (min) | % Complex in Solution to be Spread | % Silicone B in Spreading Solution | 1 Week Spread Diameter | 1 Week Spread Diameter St Dev (mm) | 5 Weeks Spread diameter (mm) | 5 Weeks Spread Diameter St Dev (mm) |
|---|---|---|---|---|---|---|---|---|
| 48 | DI water | | | 0 | 4.8 | 0.4 | 5.0 | 0.0 |
| 49 | Urea Complex - Dry | 45 | 0.75 | 0.0375 | 28.8 | 1.2 | 30.8 | 5.0 |
| 50 | Urea Complex - Wet | 25 | 0.75 | 0.0375 | 24 | 0.9 | 26 | 5.6 |
| 51 | Silwet 408 | | 0.375 | 0.0375 | 27.7 | 4.8 | 26.3 | 6.3 |

TABLE 8

Urea Complex Spray-Drift Results

| Example | Test Sample Description | % Sample Evaluated | % Urea | % Silicone B | PAM-PAA | Average Spray Drift (drops/ 0.125 cm2) | St Dev (drops/ 0.125 cm2) |
|---|---|---|---|---|---|---|---|
| 52 | DI water | | | | | 29.6 | 4.0 |
| 53 | urea complex, dry (Example 49) | 1.00 | 0.94 | 0.05 | 0.010 | 6.1 | 0.5 |
| 54 | urea complex, dry (Example 49) | 1.60 | 1.50 | 0.08 | 0.016 | 3.9 | 1.0 |
| 55 | Urea complex, wet (Example 50) | 1.00 | 0.94 | 0.05 | 0.010 | 5.2 | 1.2 |
| 56 | 1.0% PAM-PAA-Na | 1.00 | 0 | 0 | 0.010 | 1.7 | 0.1 |
| 57 | DI water | | | | | 23.2 | 8.2 |

The spray-drift data presented in Table 8 demonstrate that aqueous solutions of both the dry complex (Examples 53 and 54) and the wet complex (Example 55) reduced spray drift by approximately 75% in comparison with the water controls (Examples 52 and 57) and produced only slightly more drift than the PAM-APP-Na control solution (Example 56).

EXAMPLES 58-75

Employing either the solvent solution procedure or the molten urea-based complex-forming component (i) procedure described above and illustrated in the examples, the antidrift compositions of Table 9 below further illustrating the invention can be prepared:

TABLE 9

Additional Antidrift Compositions

| Example | % Urea-based Complex-forming Component (i) | % Antidrift Component (ii) | % Optional Superspreader Adjuvant Component (iii) | % Optional Additional Adjuvant Component(s) (iii) |
|---|---|---|---|---|
| 58 | 90% urea | 5% HPG[1] | 5% silicone A | — |
| 59 | 83% urea | 10% CMHPG[2] | 7% silicone A | — |
| 60 | 93% thiourea | 1% PAM-PAA | 3% silicone A | 3% nonionic surfactant[5] |
| 61 | 47% urea; 47% thiourea | 1% PAM-PAA | 2.5% Silicone B | 2.5% anionic surfactant[6] |
| 62 | 62% urea; 30% urea formaldehyde | 2% PAM | — | 3% nonionic surfactant[5] 3% latex sticker[5] |
| 63 | 70% urea; 21% urea formaldehyde | 1.5% PAM-PAA-Na | 7.5% Silicone C[3] | — |
| 64 | 93.5% urea hydrate | 1% PAM | 5% Silicone C | 0.5% silicone antifoam[7] |
| 65 | 90% urea hydrate | 5% xanthan gum | 4% Silicone C | 1% tallow amine |
| 66 | 40% urea; 50% urea hydrate | 1% PAM-PAA | 6% Silicone C | 3% anionic surfactant[6] |
| 67 | 89.5% urea phosphate | 2% PAM-PAA-Na | 8% Silicone C | 0.5% silicone antifoam[7] |
| 68 | 92% urea phosphate | 1% PAM-PAA-Na | 5% Silicone D[4] | 2% latex sticker |
| 69 | 80% urea; 12.8% urea phosphate | 1.2% PAM-PAA-Na | 6% Silicone D | — |
| 70 | 93.5% urea sulfate | 1.5% PAM | 5% Silicone D | — |
| 71 | 91% urea sulfate | 1.5% PAM | 7.5% Silicone D | — |
| 72 | 45% urea; 45% urea sulfate | 1.5% PAM-PAA | 4.5% Silicone A | 4% trimethylinonanol ethoxylate[8] |
| 73 | 70% urea phosphate; 24% urea sulfate | 1% PAM-PAA | 2.5% Silicone B | 2.5% alkylpolyglucoside[9] |
| 74 | 33% urea hydrate; 60% urea phosphate | 0.9% PAM-PAA-Na | 6% Silicone A | 0.1% silicone antifoam[10] |
| 75 | 80% urea hydrate; 11% urea sulfate | 1.4% PAM-PAA-Na | 7.5% Silicone A | 0.1% sodium silicate |

[1]HPG = hydroxypropyl guar
[2]CMHPG = carboxymethyl hydroxypropyl guar
[3]Silicone C = hydrolysis-resistant disiloxane superspreader surfactant
[4]Silicone D = hydrolysis-resistant trisiloxane superspreader surfactant
[5]Triton X-100 (Dow)
[6]Sodium dodecyl sulfate
[7]Sag 47, Momentive Performance Materials Inc.
[8]TMN-6 Dow
[9]Lutensol GD 70, BASF
[10]Antifoam OR90, Momentive Performance Materials Inc.

While the invention has been described with reference to particular embodiments, those skilled in the art will understand that various changes may be made and equivalents may be substituted for elements thereof without departing from the scope of the invention. It is intended that the invention not be limited to the particular embodiments disclosed but that it include all embodiments falling within the scope of the appended claims.

The invention claimed is:

1. A solid, water-soluble, fast-dissolving antidrift composition which comprises a urea-based complex-forming component (i) complexed with at least a portion of an antidrif component (ii), and as adjuvant component (iii) a superspreader surfactant with all, some or none of the superspreader surfactant being complexed with urea-based complex-forming component (i).

2. The antidrift composition of claim 1 wherein the superspreader surfactant is at least one organosilicon surfactant selected from the group consisting of polysiloxane alkoxylate surfactant (I), hydrolysis-resistant carbosilance surfactannt (IV), hydrolysis-resistant disiloxane surfactant (VII), first hydrolysis-resistant trisiloxane surfactant (IX), second hydrolysis-resistant trisiloxane surfactant (XI) and third hydrolysis-resistant trisiloxane (XIV) as hereinafter defined:

polysiloxane alkoxylate surfactant of general formula (I):

$$(R^1R^2R^3SiO_{1/2})(R^4R^5SiO_{2/2})_n(R^6R^{10}SiO_{2/2})_p(R^7R^8R^9SiO_{1/2}) \quad (I)$$

wherein n is 0 or 1; p is 1 or 2; $R^1$ to $R^8$ are methyl; $R^9$ is methyl or, when $R^{10}$ is methyl, $R^9$ is $R^{11}$; $R^{10}$ is methyl or $R^{11}$ with $R^{11}$ being a polyalkylene oxide group of general formula (II):

$$R^{13}(C_2H_4O)_w(C_3H_6O)_x(C_4H_8O)_yR^{12} \quad (II)$$

in which w, x and y are independently an integer from 0 to 20, with the proviso that w is greater than or equal to 2 and w+x+y is in a range of from 2 to 20; $R^2$ is a hydrogen atom, an aliphatic radical or an acetyl group; and, $R^{13}$ is a divalent aliphatic radical having the structure (III):

$$—CH_2CH(R^{14})(R^{15})_zO— \quad (III)$$

in which $R^{14}$ is a hydrogen atom or an aliphatic radical, $R^{15}$ is a divalent aliphatic radical of 1 to 6 carbon atoms and z is 0 or 1;

hydrolysisis-resistant carbosilane surfactants of general formula (IV):

$$(R^{16})(R^{17})(R^{18})Si—R^{19}—Si(R^{20})(R_{21})(R^{22}) \quad (IV)$$

wherein $R^{16}$, $R^{17}$, $R^{18}$, $R^{20}$ and $R^{21}$ are each independently selected from the group consisting of 1 to 6 monovalent hydrocarbon radicals, aryl and a hydrocarbon group of 7 to 10 carbon atoms containing an aryl group; $R^{19}$ is a divalent hydrocarbon group of 1 to 3 carbons; $R^{22}$ is a polyalkylene oxide group of general formula (V):

$$R^{23}(C_2H_4O)_d(C_3H_6O)_e(C_4H_8O)_fR^{24} \quad (V)$$

in which $R^{23}$ is a divalent linear or branched hydrocarbon radical having structure (VI):

$$—CH_2CH(R^{25})(R^{26})_gO— \quad (VI)$$

in which $R^{25}$ is hydrogen or methyl; $R^{26}$ is a divalent alkyl radical of 1 to 6 carbon atoms where the subscript g may be 0 or 1; $R^{24}$ is selected from the group consisting of hydrogen, monovalent hydrocarbon radical of 1 to 6 carbon atoms and acetyl, subject to the limitation that subscripts d, e and f are zero or positive and satisfy the following relationships:

$$2 \le d+e+f \le 20 \text{ with } d \ge 2;$$

hydrolysis-resistant disiloxane surfactants of general formula (VII):

$$MM' \quad (VII)$$

wherein M is $R^{27}R^{28}R^{29}SiO_{1/2}$ and M' is $R^{30}R^{31}R^{32}SiO^{1/2}$ in which $R^{27}$ is selected from the group consisting of branched monovalent hydrocarbon radical of from 3 to 6 carbon atoms or $R^{33}$ in which $R^{33}$ is selected from the group consisting of $R^{34}R^{35}R^{36}SiR^{37}$ and $(R^{30}R^{31}R^{32})SiR^{37})$ in which $R^{34}$, $R^{35}$ and $R^{36}$ each independently is selected from the group consisting of monovalent hydrocarbon radical of from 1 to 6 carbon atoms and monovalent aryl or alkaryl hydrocarbon radical of from 6 to 13 carbon atoms and $R^{37}$ is a divalent hydrocarbon radical of from 1 to 3carbon atoms; $R^{28}$ and $R^{29}$ each independently is selected from the group consisting of monovalent hydrocarbon radical of from 1 to 6 carbon atoms or $R^{27}$, and $R^{30}$ is a polyalkylenc oxide group selected from the group consisting of $R^{38}(C_2H_4O)_a(C_3H_6O)_b(C_4H_8O)_cR^{39}$ and $R^{37}SiR^{31}R^{32}(R^{38}(C_2H_4O)_a(C_3H_6O)_b(C_4H_8O)_cR^{39})$ in which $R^{38}$ is a divalent linear or branched hydrocarbon radical having the structure (VIII):

$$—CH_2CH(R^{40})(R^{41})_dO— \quad (VIII)$$

in which $R^{40}$ is hydrogen or methyl; $R^{41}$ is a divalent alkyl radical of 1 to 6 carbon atoms in which subscript d may be 0 or 1; $R^{39}$ is selected from the group consisting of hydrogen, monovalent hydrocarbon radical of from 1 to 6 carbon atoms and acetyl subject to the limitation that subscripts a, b and c are zero or positive and satisfy the following relationships:

$$2 \le a+b+c \le 20 \text{ with } a \ge 2,$$

and $R^{31}$ and $R^{32}$ each independently is selected from the group of monovalent hydrocarbon radicals having from 1 to 6 carbon atoms or $R^{30}$;

first hydrolysis-resistant trisiloxane of general formula (IX):

$$M^1D^1M^2 \quad (IX)$$

wherein $M^1$ is $(R^{42})(R^{43})(R^{44})SiO_{1/2}$, $M^2$is $(R^{45})(R^{46})(R^{47})SiO_{1/2}$ and $D^1$ is $(R^{48})(Z)SiO_{2/2}$ in which $R^{42}$ is selected from a branched or linear hydrocarbon group of from 2 to 4 carbon atoms, aryl and alkyl hydrocarbon group of 4 to 9 carbon atoms containing an aryl substituent of 6 to 20 carbon atoms; $R^{43}$, $R^{44}$, $R^{45}$,$R^{46}$, $R^{47}$ and $R^{48}$ each independently is selected from the group consisting of monovalent hydrocarbon radical of 1 to 4 carbon atoms and hydrocarbon radical of 4 to 9 carbons containing an aryl group of from 6 to 20 carbon atoms, and Z is an alkyleneoxide group of general formula (X):

$$R^{49}(C_2H_4O)_a(C_3H_6O)_b(C_4H_8O)_cR^{50} \quad (X)$$

in which $R^{49}$ is a linear or branched divalent hydrocarbon radical of 2, 3, 5, 6, 7, 8 or 9 carbon atoms; $R^{50}$ is selected from the group consisting of hydrogen, monovalent hydrocarbon radicals of from 1 to 6 carbon atoms and acetyl, and in which the subscripts a, b and c are zero or positive and satisfy the following relationships:

$$2 \le a+b+c \le 20 \text{ with } a \ge 2;$$

second hydrolysis-resistant trisiloxane of general formula (XI):

$$M^3D^2M^4 \quad (XI)$$

wherein $M^3$ is $(R^{51})(R^{52})(R^{53})SiO_{1/2}$, $M^4$ is $R^{54})(R^{55})(R^{56})SiO_{1/2}$ and $D^2$ is $(R^{57})(Z')SiO_{2/2}$ in which $R^{51}$, $R^{52}$, $R^{53}$,$R^{54}$, $R^{55}$, $R^{56}$ and $R^{57}$ each independently is selected from the group consisting of monovalent hydrocarbon radical of 1 to 4 carbon atoms, aryl and alkyl hydrocarbon group of 4 to 9 carbon atoms containing an aryl substituents of 6 to 20 carbon atoms; Z' is a polyalkylene oxide group of general formula (XII):

$$R^{58}(C_2H_4O)_d(C_3H_6O)_e(C_4H_8O)_fR^{59} \quad (XII)$$

in which $R^{58}$ is selected from a branched or linear divalent hydrocarbon radical of the general formula (XIII):

$$—C_4H_8O(C_2H_4O)— \quad (XIII)$$

in which $R^{59}$ is selected from the group consisting of hydrogen, monovalent hydrocarbon radical of from 1 to 6 carbon atoms and acetyl, and in which the subscripts d, e and f are zero or positive and satisfy the following relationships:

$$2 \le d+e+f \le 20 \text{ with } d \ge 2; \text{ and,}$$

third hydrolysis-resistant trisiloxane of general formula (XIV):

$$M^5D^3M^6 \quad (XIV)$$

wherein $M^5$ is $(R^{60})(R^{61})(R^{62})SiO_{1/2}$, $M^6$ is $(R^{63})(R^{64})(R^{65})SiO_{1/2}$ and $D^3$ is $(R^{66})(Z'')SiO_{2/2}$ in which $R^{60}$, $R^{61}$, $R^{62}$, $R^{63}$, $R^{64}$ and $R^{65}$ each independently is selected from the group consisting of monovalent hydrocarbon radical of 1 to 4 carbon atoms, aryl, and alkyl hydrocarbon group of 4 to 9 carbon atoms containing an aryl substituent of 6 to 20 carbon atoms, $R^{66}$ is a linear or branched hydrocarbon radical of 2 to 4 carbons; Z" is a polyalkylene oxide group of general formula (XV):

$$R^{67}(C_2H_4O)_g(C_3H_6O)_h(C_4H_8O)_iR^{68} \quad (XV)$$

wherein $R^{67}$ is a linear or branched divalent hydrocarbon radical of 2, 3, 5, 6, 7, 8, or 9 carbon atoms; $R^{68}$ is selected from the group consisting of hydrogen, monovalent hydrocarbon radical of from 1 to 6 carbon atoms and acetyl, and in which subscripts g, h and i are zero or positive and satisfy the following relationships:

$$2 \le g+h+i \le 20 \text{ with } g \ge 2.$$

3. The antidrift composition of claim 1 further comprising at least one adjuvant component (iii) selected from the group consisting of organosilicon superspreader surfactant, non-organosilicon superspreader surfactant, non-superspreading organosilicon surfactant, non-superspreading, non-organosilicon surfactant, antifoam additive, anticaking/free flow additive, sticker and dye.

4. The antidriti composition of claim 1 further comprising as adjuvant component (iii) at least one mixture of surfactants selected from the group consisting of organosilicon superspreader surfactant and non-organosilicon superspreader surfactant; organosilicon superspreader surfactant and non-superspreading organosilicon surfactant; organosilicon superspreader surfactant and non-superspreading, non-organosilicon surfactant; non-organosilicon superspreader surfactant and non-superspreading organosilicon surfactant; non-organosilicon superspreader surfactant and non-superspreading, non-organosilicon surfactant; and, non-superspreading organosilicon surfactant and non-superspreading, non-organosilicon surfactant, with all, some or none of a mixture, or a surfactant component of a mixture, being complexed with urea-based complex-forming component (i).

5. The antidrift composition of claim 4 wherein the non-organosilicon surthetant is of general formula (XVI):

(XVI)

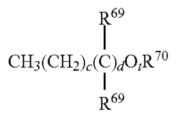

wherein $R^{69}$ is the same or different and is selected from the group consisting of hydrogen and an alkyl of 1 to 4 carbon atoms; c is 5 to 9, d is 0 to 4, c+d is 5 to 9 and t is 0 or 1; $R^{70}$ is a nonionic hydrophilic moiety with the proviso that when t is 0, $R^{70}$ is

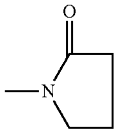

and when t is 1, $R^{70}$ is selected from the group consisting of (i) $[C_2H_4O]_f[C_3H_6O]_gH$ and (ii) $(C_6H_9O_5)_h—C_6H_{10}O_5$ in which f is 1 to 40, g is 0 to 40 and h is 1 to 4.

6. The antidrill composition of claim 5 wherein the non-organosilicon surfactant is admixed with an organosilicon superspreader surfactant and/or non-organosilicon superspreader surfactant.

7. A solid, water-soluble, fast-dissolving antidrift composition which comprises a urea-based complex-forming component (i) which is at least one member selected from the group consisting of urea, thiourea, urea formaldehyde, urea hydrate, urea phosphate and urea sulfate complexed with an antidrift component (ii) which is at least one member selected from the group consisting of guar, guar derivative, xantham gum, polyacrylamide homopolymer and polyacrylamide copolymer, the antidrift composition optionally including at least one adjuvant component (iii) selected from the group consisting of organosilicon superspreader surfactant, non-organosilicon superspreader surfactant, non-superspreading organosilicon surfactant, non-superspreading, non-organosilicon surfactant, antifoam additive, anticakingifree flow additive, sticker and dye.

8. The antidrift composition of claim 7 further complexed with, as adjuvant component (iii), an organosilicon superspreader surfactant selected from the group consisting of polysiloxane alkoxylate surfactant (I), hydrolysis-resistant carbosilane surfactant (IV), hydrolysis-resistant disiloxane surfactant (VII), first hydrolysis-resistant trisiloxane surfactant (IX), second hydrolysis-resistant trisiloxane surfactant (XI) and third hydrolysis-resistant trisiloxane (XIV) as hereinafter defined:

polysiloxane alkoxylate surfactant of general formula (I):

$$(R^1R^2R^3SiO_{1/2})(R^4R^5SiO_{2/2})_n(R^6R^{10}SiO_{2/2})_p(R^7R^8R^9SiO_{1/2}) \quad (I)$$

wherein n is 0 or 1; p is 1 or 2; $R^1$ to $R^8$ are methyl; $R^9$ is methyl or, when $R^{10}$ is methyl, $R^9$ is $R^{11}$; $R^{10}$ is methyl or $R^{11}$ with $R^{11}$ being a polyalkylene oxide group of general formula (II):

$$R^{13}(C_2H_4O)_w(C_3H_6O)_x(C_4H_8O)_yR^{12} \quad (II)$$

in which w, x and y are independently an integer from 0 to 20, with the proviso that w is greater than or equal to 2 and w+x+y is in a range of from 2 to 20; $R^{12}$ is a hydrogen atom, an aliphatic radical or an acetyl group; and, $R^{13}$ is a divalent aliphatic radical having the structure(III):

$$—CH_2CH(R^{14})(R^{15})_zO— \quad (III)$$

in which $R^{14}$ is a hydrogen atom or an aliphatic radical, $R^{15}$ is a divalent aliphatic radical of 1 to 6 carbon atoms and z is 0 or 1;

hydrolysisis-resistant carbosilane surfactants of general formula (IV):

$$(R^{16})(R^{17})(R^{18})Si—R^{19}—Si(R^{20})(R^2)(R^{22}) \quad (IV)$$

wherein $R^{16}$, $R^{17}$, $R^{18}$, $R^{20}$ and $R^{21}$ are each independently selected from the group consisting of 1 to 6 monovalent hydrocarbon radicals, aryl and a hydrocarbon group of 7 to 10 carbon atoms containing an aryl group; $R^{19}$ is a divalent hydrocarbon group of 1 to 3 carbons; $R^{22}$ is a polyalkvlene oxide group of general formula (V):

$$R^{23}(C_2H_4O)_d(C_3H_6O)_e(C_4H^8O)_fR^{24} \quad (V)$$

in which $R^{23}$ is a divalent linear or branched hydrocarbon radical having structure (VI):

$$—CH_2CH(R^{25})(R^{26})_gO— \quad (VI)$$

in which $R^{25}$ is hydrogen or methyl; $R^{26}$ is a divalent alkyl radical of 1 to 6 carbon atoms where the subscript g may be 0 or 1; $R^{24}$ is selected from the group consisting of hydrogen, monovalent hydrocarbon radical of 1 to 6 carbon atoms and acetyl, subject to the limitation that subscripts d, e and f are zero or positive and satisfy the following relationships:

$$2 \leq d+e+f \leq 20 \text{ with } d \geq 2;$$

hydrolysis-resistant disiloxane surfactants of general formula (VII):

$$MM' \quad (VII)$$

wherein M is $R^{27}R^{28}R^{29}SiO_{1/2}$ and M' is $R^{30}R^{31}R^{32}SiO^{1/2}$ in which $R^{27}$ is selected from the group consisting of branched monovalent hydrocarbon radical of from 3 to 6 carbon atoms or $R^{33}$ in which $R^{33}$ is selected from the group consisting of $R^{34}R^{35}R^{36}SiR^{37}$ and $(R^{30}R^{31}R^{32})SiR^{37})$ in which $R^{34}$, $R^{35}$ and $R^{36}$ each independently is selected from the group consisting of monovalent hydrocarbon radical of from 1 to 6 carbon atoms and monovalent aryl or alkaryl hydrocarbon radical of from 6 to 13 carbon atoms and $R^{37}$ is a divalent hydrocarbon radical of from 1 to 3 carbon atoms; $R^{28}$ and $R^{29}$ each independently is selected from the group consisting of monovalent hydrocarbon radical of from 1 to 6 carbon atoms or $R^{27}$, and $R^{30}$ is a polyalkylene oxide group selected from the group consisting of $R^{38}(C_2H_4O)_a(C_3H_6O)_b(C_4H_8O)_cR^{39}$ and $R^{37}SiR^{31}R^{32}(R^{38}(C_2H_4O)_a(C_3H_6O)_b(C_4H_8O)_cR^{39})$ in which $R^{38}$ is a divalent linear or branched hydrocarbon radical having the structure (VIII):

$—CH_2CH(R^{40})(R^{41})_dO$—tm (VIII)

in which $R^{40}$ is hydrogen or methyl; $R^{41}$ is a divalent alkyl radical of 1 to 6 carbon atoms in which subscript d may be 0 or 1; $R^{39}$ is selected from the group consisting of hydrogen, monovalent hydrocarbon radical of from 1 to 6 carbon atoms and acetyl subject to the limitation that subscripts a, b and c are zero or positive and satisfy the following relationships:

$2 \le a+b+c \le 20$ with $a \ge 2$, and $R^{31}$ and $R^{32}$ each independently is selected from the group of monovalent hydrocarbon radicals having from 1 to 6 carbon atoms or $R^{30}$;

first hydrolysis-resistant trisiloxane of general formula (IX):

$M^1D^1M^2$ (IX)

wherein $M^1$ is $(R^{42})(R_{43})(R_{44})SiO_{1/2}$, $M^2$ is $(R^{45})(R_{46})(R^{47})SiO_{1/2}$ and $D^1$ is $(R^{48})(Z)SiO_{2/2}$ in which $R^{42}$ is selected from a branched or linear hydrocarbon group of from 2 to 4 carbon atoms, aryl and alkyl hydrocarbon group of 4 to 9 carbon atoms containing an aryl substituent of 6 to 20 carbon atoms; $R^{43}$, $R^{44}$, $R^{45}$, $R^{46}$, $R^{47}$ and $R^{48}$ each independently is selected from the group consisting of monovalent hydrocarbon radical of 1 to 4 carbon atoms and hydrocarbon radical of 4 to 9 carbons containing an aryl group of from 6 to 20 carbon atoms, and Z is an alkyleneoxide group of general formula (X):

$R^{49}(C_2H_4O)_a(C_3H_6O)_b(C_4H_8O)_cR^{50}$ (X)

in which $R^{49}$ is a linear or branched divalent hydrocarbon radical of 2, 3, 5, 6, 7, 8 or 9 carbon atoms; $R^{50}$ is selected from the group consisting of hydrogen, monovalent hydrocarbon radicals of from 1 to 6 carbon atoms and acetyl, and in which the subscripts a, b and c are zero or positive and satisfy the following relationships:

$2 \le a+b+c \le 20$ with $a \ge 2$;

second hydrolysis-resistant trisiloxane of general formula (XI):

$M^3D^2M^4$ (XI)

wherein $M^3$ is $(R^{51})(R^{52})(R^{53})SiO_{1/2}$, $M^4$ is $(R^{54})(R^{55})(R^{56})SiO_{1/2}$ and $D^2$ is $(R^{57})(Z')SiO_{2/2}$ in which $R^{51}$, $R^{52}$, $R^{53}$, $R^{54}$, $R^{55}$, $R^{56}$ and $R^{57}$ each independently is selected from the group consisting of monovalent hydrocarbon radical of 1 to 4 carbon atoms, aryl and alkyl hydrocarbon group of 4 to 9 carbon atoms containing an aryl substituents of 6 to 20 carbon atoms; Z' is a polyalkylene oxide group of general formula (XII):

$R^{58}(C_2H_4O)_d(C_3H_6O)_e(C_4H_8O)_fR^{59}$ (XII)

in which $R^{58}$ is selected from a branched or linear divalent hydrocarbon radical of the general formula (XIII):

$—C_4H_8O(C_2H_4O)—$ (XIII)

in which $R^{59}$ is selected from the group consisting of hydrogen, monovalent hydrocarbon radical of from 1 to 6 carbon atoms and acetyl, and in which the subscripts d, e and f are zero or positive and satisfy the following relationships:

$2 \le d+e+f \le 20$ with $d \ge 2$; and, third hydrolysis-resistant trisiloxanc of general formula (XIV):

$M^5D^3M^6$ (XIV)

wherein $M^5$ is $(R^{60})(R^{61})(R^{62})SiO_{1/2}$, $M^6$ is $(R^{63})(R^{64})(R^{65})SiO_{1/2}$ and $D^3$ is $(R^{66})(Z'')SiO_{2/2}$ in which $R^{60}$, $R^{61}$, $R^{62}$, $R^{63}$, $R^{64}$ and $R^{65}$ independently is selected from the group consisting of monovalent hydrocarbon radical of 1 to 4 carbon atoms, aryl, and alkyl hydrocarbon group of 4 to 9 carbon atoms containing an aryl substituent of 6 to 20 carbon atoms, $R^{66}$ is a linear or branched hydrocarbon radical of 2 to 4 carbons; Z" is a polyalkylene oxide group of general formula (XV):

$R^{67}(C_2H_4O)_g(C_3H_6O)_h(C_4H_8O)_iR^{68}$ (XV)

wherein $R^{67}$ is a linear or branched divalent hydrocarbon radical of 2, 3, 5, 6, 7, 8, or 9 carbon atoms; $R^{68}$ is selected from the group consisting of hydrogen, monovalent hydrocarbon radical of from 1 to 6 carbon atoms and acetyl, and in which subscripts g, h and i are zero or positive and satisfy the following relationships:

$2 \le g+h+i \le 20$ with $g \ge 2$.

9. The antidrift composition of claim 8 further comprising as adjuvant component (iii) a non-organosilicon surfactant of general formula (XVI):

(XVI)

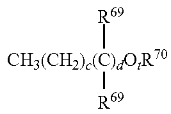

wherein $R^{69}$ is the same or different and is selected from the group consisting of hydrogen and an alkyl of from 1 to 4 carbon atoms; c is 5 to 9, d is 0 to 4, c+d is 5 to 9 and t is 0 or 1; $R^{70}$ is a nonionic hydrophilic moiety with the proviso that when t is 0, $R^{70}$ is

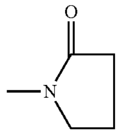

and when t is 1, $R^{70}$ is selected from the group consisting of (i) $[C_2H^4O]_f[C_3H_6O]_gH$ and (ii) $(C_6H_9O_5)_h—C_6H_{10}O_5$, in which f is 1 to 40, g is 0 to 40 and h is 1 to 4.

10. The antidrift composition of claim 7 wherein at least 50 weight percent of antidrift component (ii) is complexed with urea-based complex-forming component (i), the antidrift composition comprising an amount of complex-forming component (i), antidrift component (ii) and optional adjuvant component (iii) within one of the weight parts ranges A, B and C as hereinafter set forth:

| | Weight Parts Ranges A, B and C | | |
|---|---|---|---|
| Component | A | B | C |
| (i) | 55-99.9 | 70-95 | 80-98 |
| (ii) | 0.1-25 | 0.5-10 | 1-5 |
| (iii) | 0-20 | 1-20 | 1-15. |

11. A process for producing the solid, water-soluble, fast-dissolving antidrift composition of claim 1 which comprises forming a complex of urea-based complex-forming component (i) and antidrift component (ii), the resulting fast-dissolving antidrift composition in particulate form exhibiting a dissolution time in aqueous medium that is at least 30% less than that of an equivalent amount of non-complexed urea-based complex-thrilling component (i) and antidrift component (ii) of comparable particulate form under substantially identical dissolution conditions.

12. The process of claim 11 wherein the resulting fast-dissolving antidrift composition exhibits a dissolution time in aqueous medium that is at least 50% less than that of an equivalent amount of non-complexed urea-based complex-forming component (i) and antidrift component (ii) of comparable particulate form under substantially identical dissolution conditions.

13. The process of claim 11 wherein the resulting fast-dissolving antidrift composition exhibits a dissolution time in aqueous medium that is at least 70% less than that of an equivalent amount of non-complexed urea-based complex-forming component (i) and antidrift component (ii) of comparable particulate form under substantially identical dissolution conditions.

* * * * *